United States Patent

Groenke et al.

[11] Patent Number: 6,125,299
[45] Date of Patent: Sep. 26, 2000

[54] AED WITH FORCE SENSOR

[75] Inventors: Allen W. Groenke, Bloomington; James E. Brewer, Cottage Grove, both of Minn.

[73] Assignee: SurVivaLink Corporation, Minneapolis, Minn.

[21] Appl. No.: 09/182,831

[22] Filed: Oct. 29, 1998

[51] Int. Cl.[7] ............................. A61N 1/39; A61H 31/00
[52] U.S. Cl. ..................................... 607/6; 607/3; 600/16
[58] Field of Search ............................. 607/3, 6; 600/16, 600/587; 340/626

[56] References Cited

U.S. PATENT DOCUMENTS

| | | | |
|---|---|---|---|
| 4,273,114 | 6/1981 | Barkalow et al. | 607/3 |
| 4,619,265 | 10/1986 | Morgan et al. | 607/5 |
| 5,228,449 | 7/1993 | Christ et al. | |
| 5,484,391 | 1/1996 | Buckman, Jr. et al. | |
| 5,838,244 | 11/1998 | Schmidt et al. | |
| 5,853,292 | 12/1998 | Eggert et al. | |

*Primary Examiner*—Carl H. Layno
*Attorney, Agent, or Firm*—Patterson, Thuente & Skaar, P.A.

[57] ABSTRACT

A force sensor, for use in combination with an automated electronic defibrillator (AED), includes a first conductive layer. A second conductive layer is spaced apart from the first conductive layer such that no electrical communication occurs between the first and second conductive layers. An electrical communication device is provided for establishing electrical communication between the first and second conductive layers responsive to the application of a force to said electrical communication means. A method of prompting a rescuer in the application of cardiopulmonary resuscitation to a victim includes the steps of:

- sensing a force applied by the rescuer to the victim's sternum;
- sensing an interval between successive applications of force to the victim's sternum;
- comparing the force applied by the rescuer to the victim's sternum to a standard of force known to effect resuscitation;
- providing a prompt to the rescuer that prompts the rescuer to vary the force delivered to approximate the force that is known to effect resuscitation;
- comparing the interval between successive applications of force to the victim's sternum to a standard interval known to effect resuscitation; and
- providing a prompt to the rescuer that prompts the rescuer to vary the interval of force application to approximate the interval that is known to effect resuscitation.

27 Claims, 15 Drawing Sheets

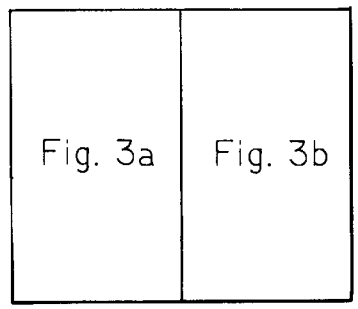
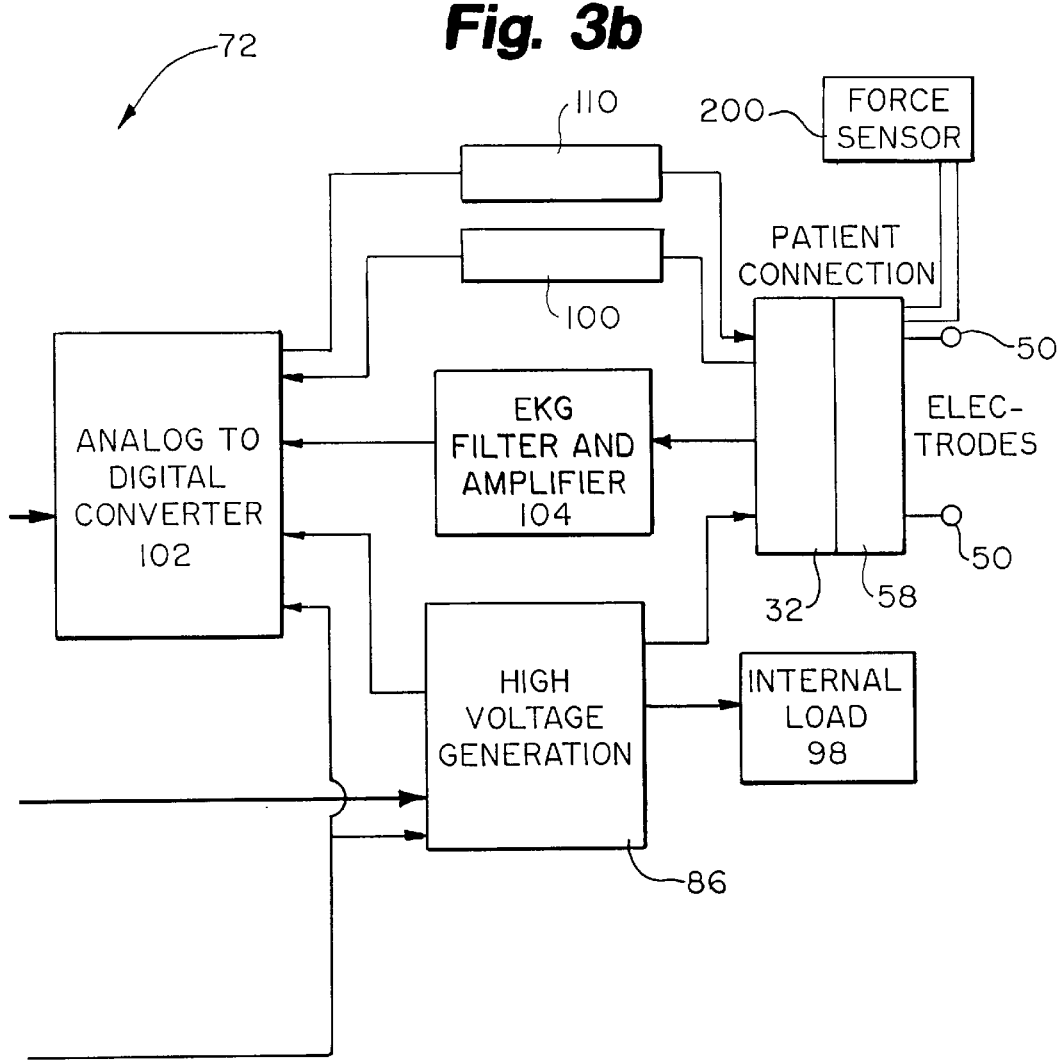

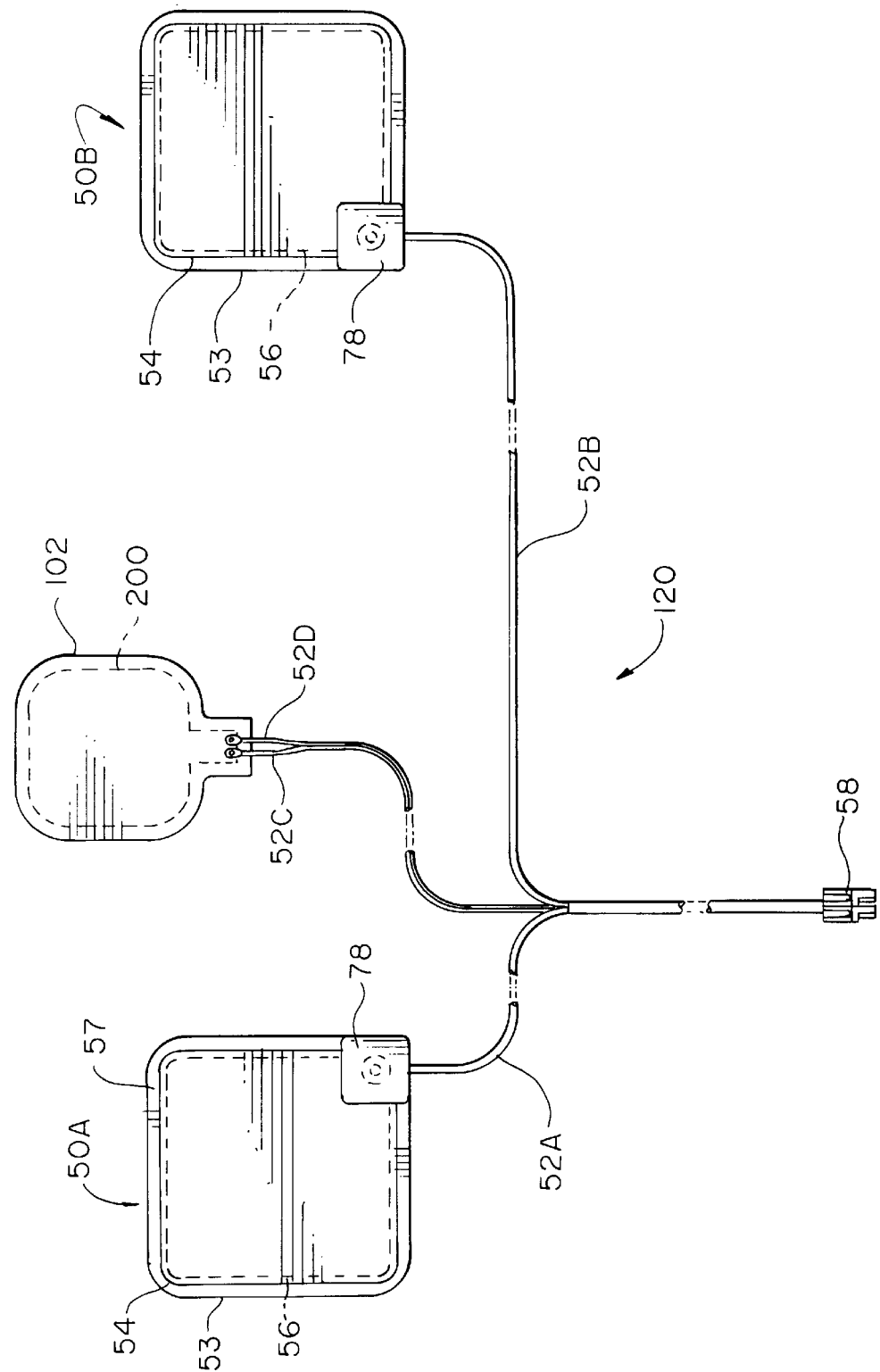

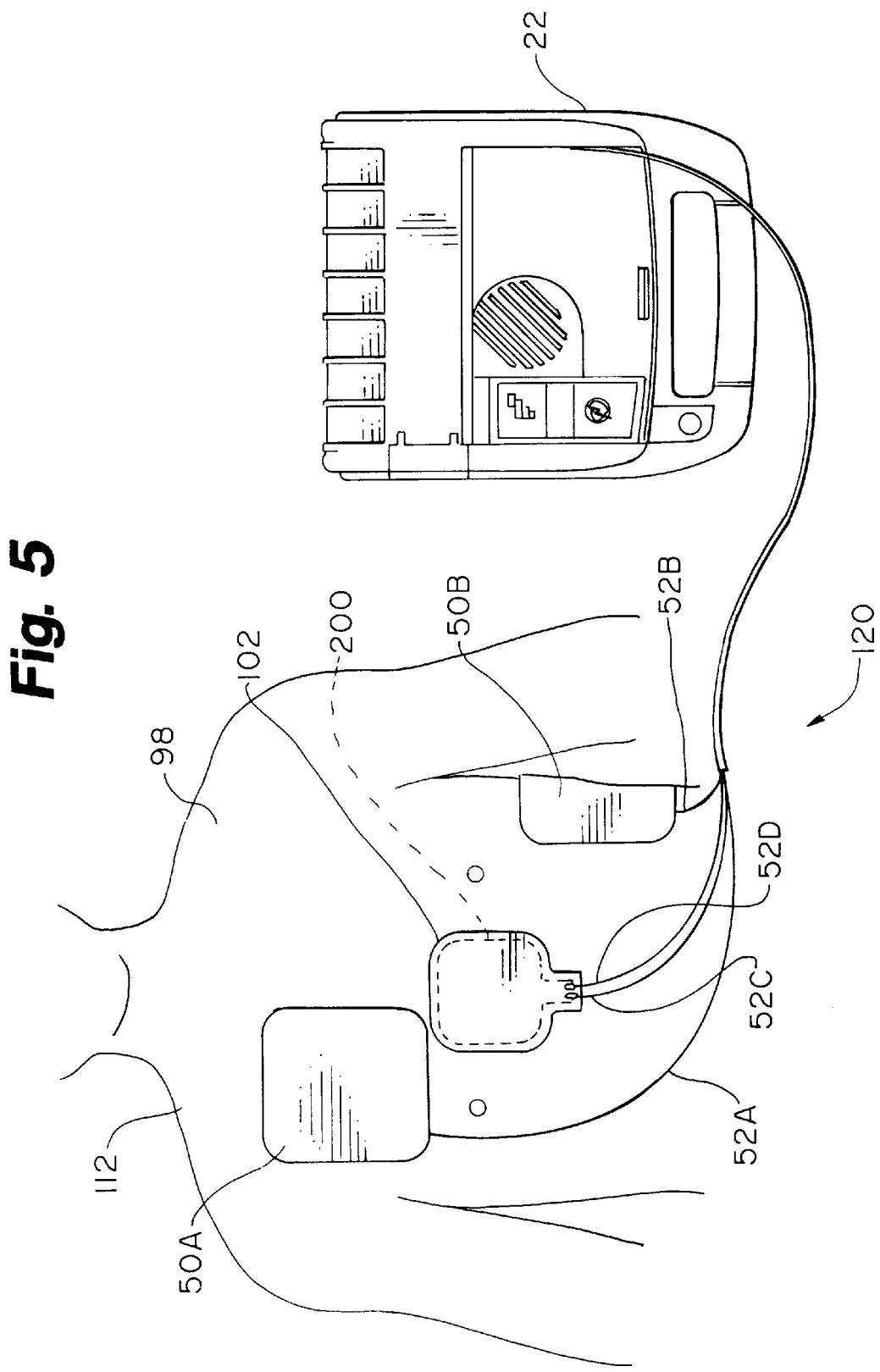

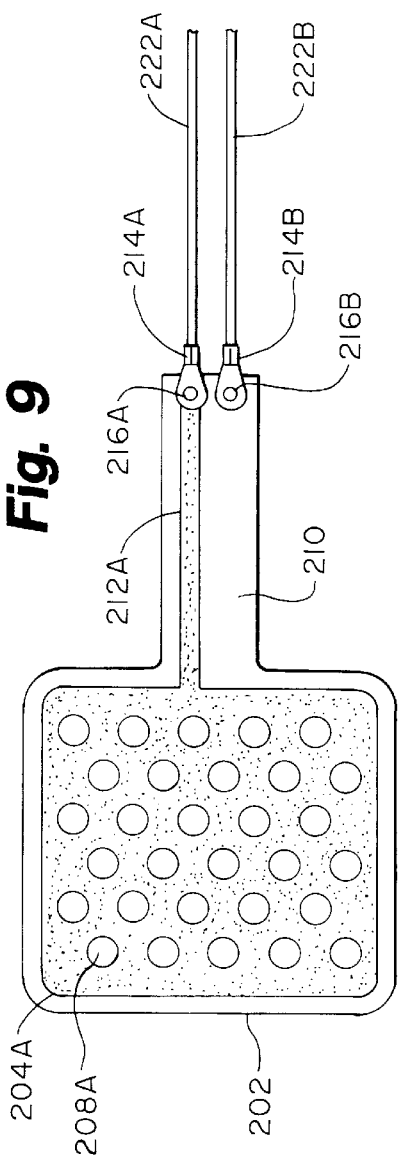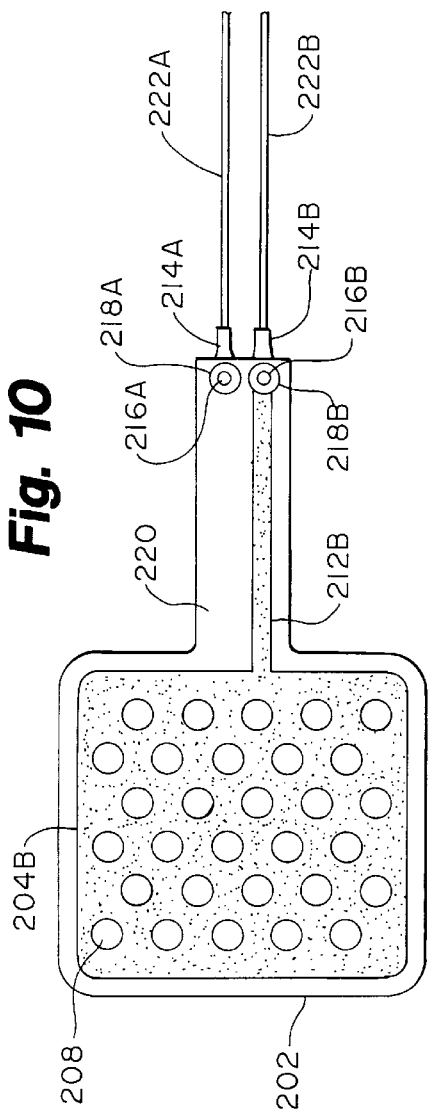

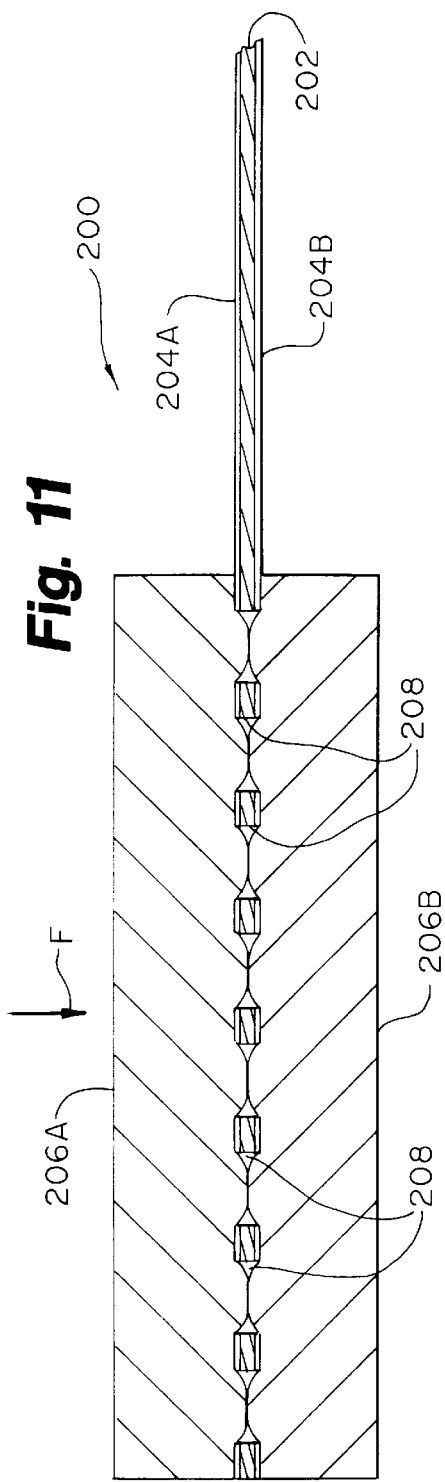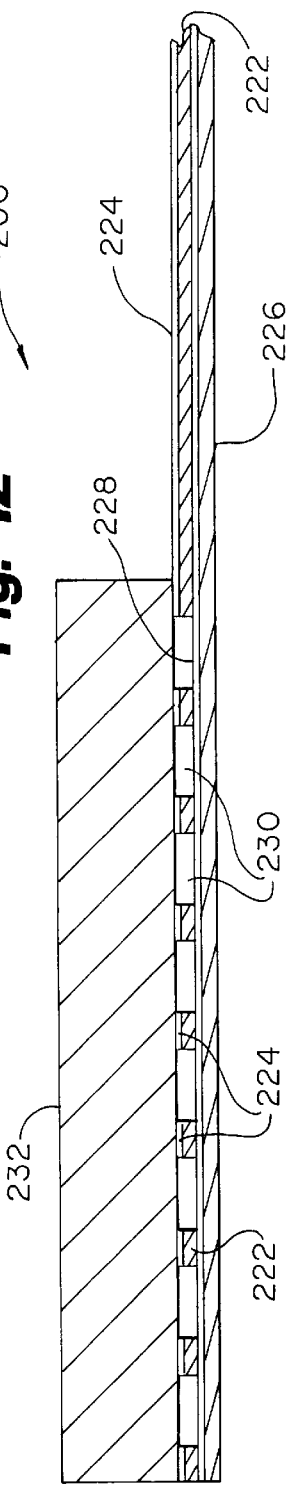

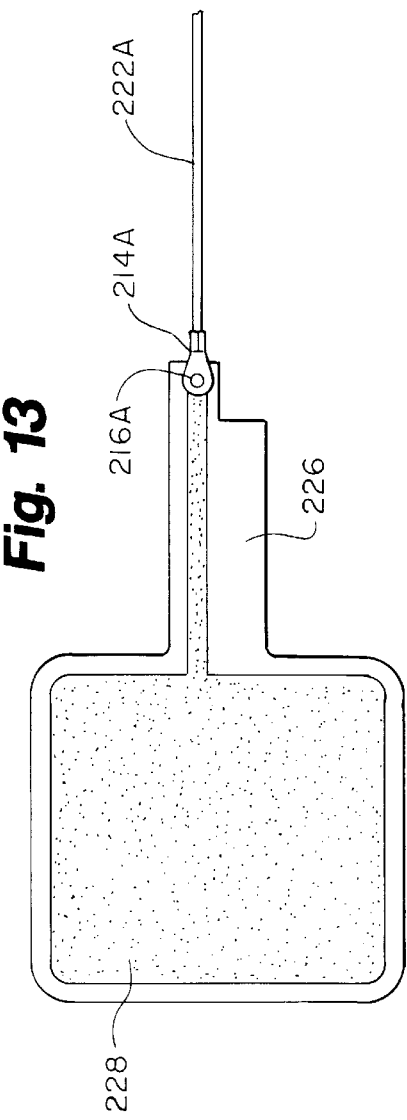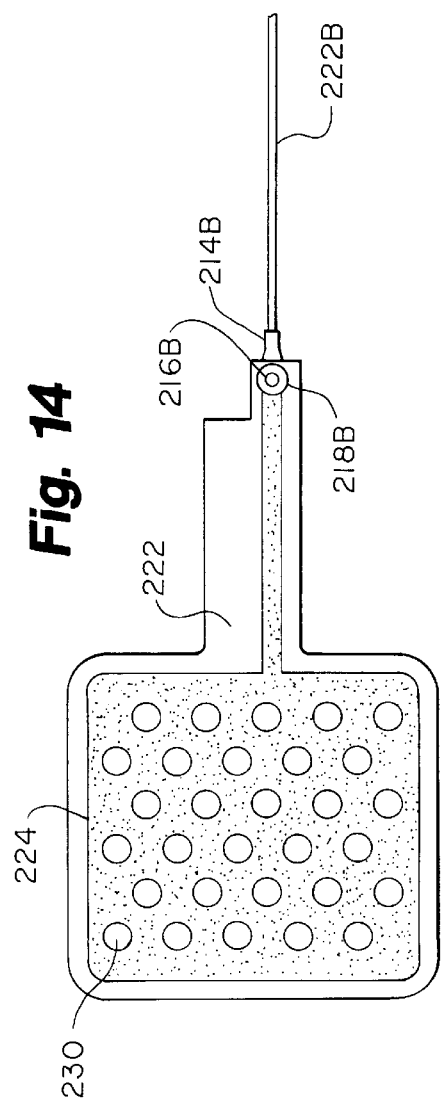

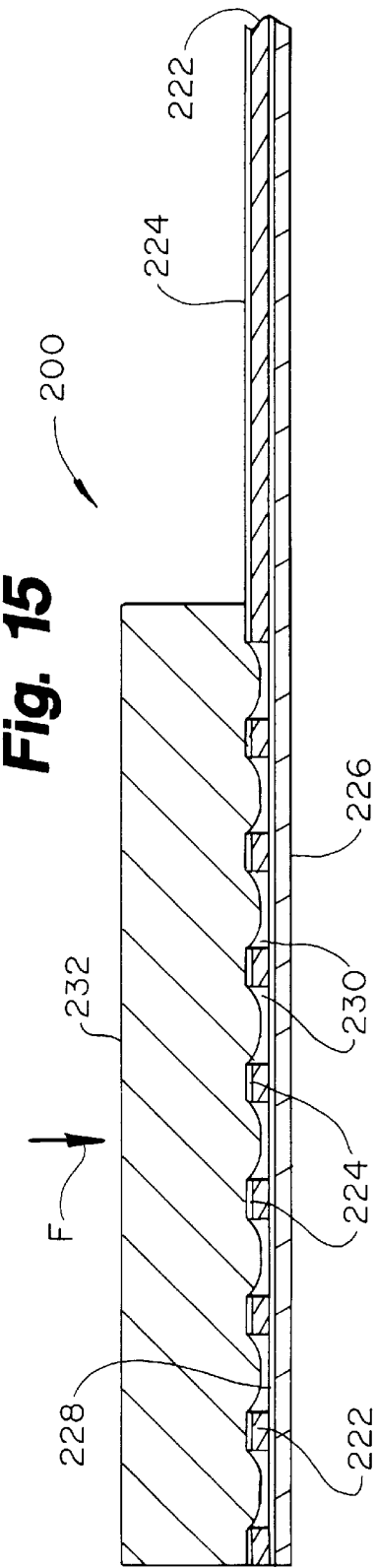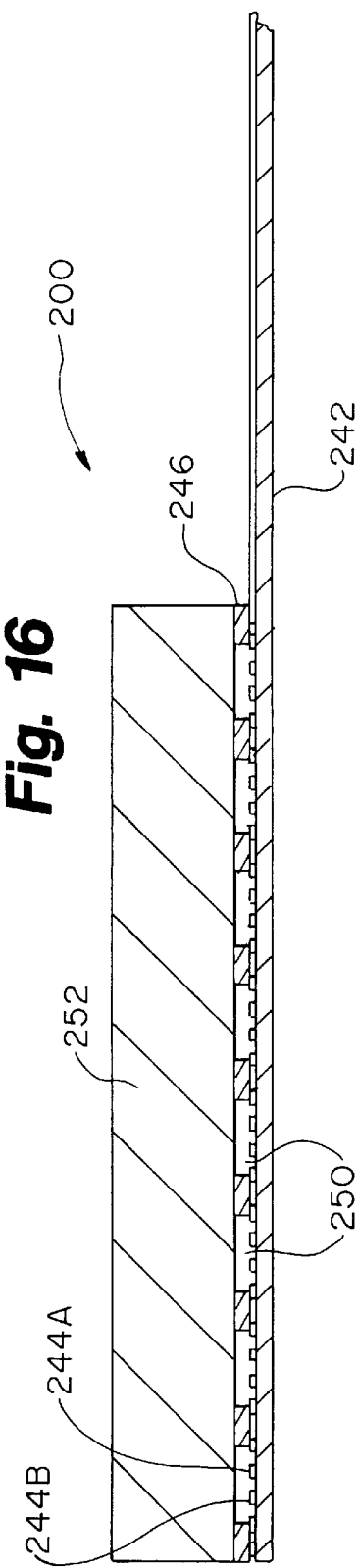

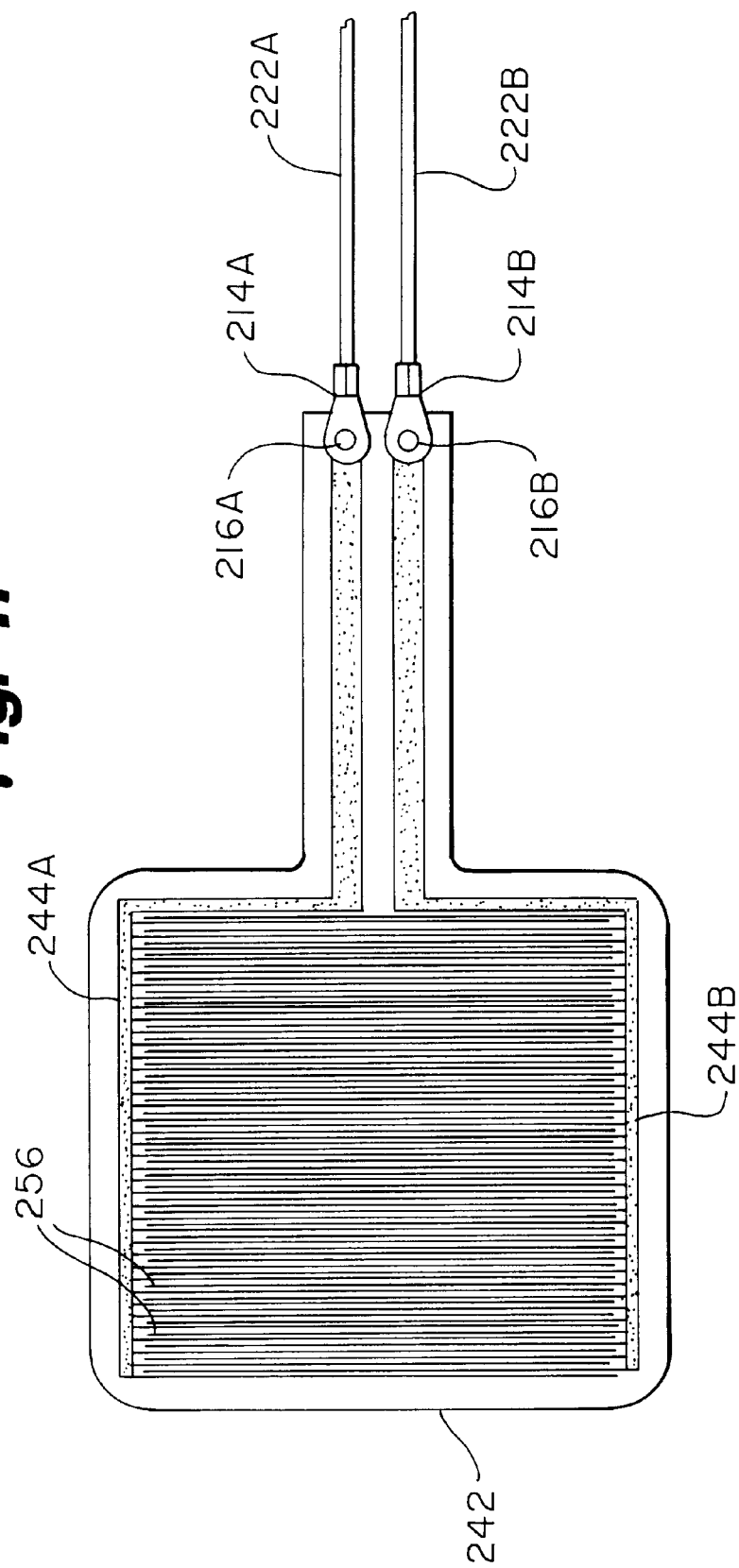

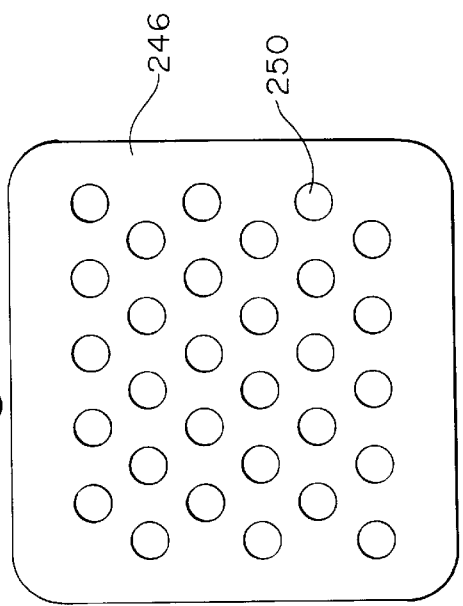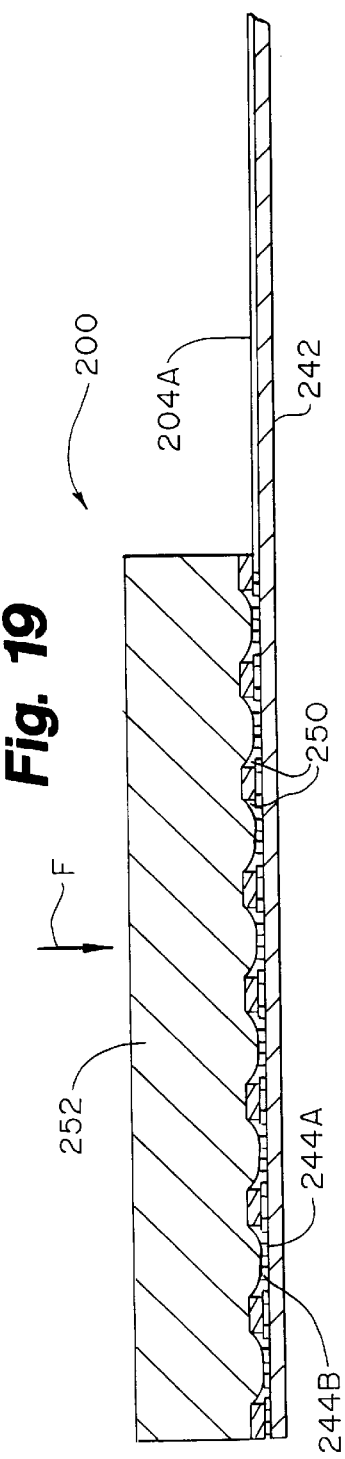

AED WITH FORCE SENSOR

TECHNICAL FIELD

The present invention relates to devices useful for assisting in the administration of cardiopulmonary resuscitation (CPR). More particularly, the present invention relates to a sensor for being disposed on the body of a victim to measure parameters related to the CPR.

BACKGROUND OF THE INVENTION

CPR is a technique used by a rescuer in an emergency situation to get oxygen into a victims blood when that persons heart has stopped beating and/or they are not breathing spontaneously. When performing CPR the rescuer creates blood circulation in the victims body by periodically compressing the victims chest.

The American Heart Association (AHA) recommends that the rescuer press down on the sternum with a force sufficient to depress it between 4 and 5 cm. The recommended rate for these periodic depressions is 100 times a minute (ILCOR Advisory Statement for Single-Rescuer Adult Basic Life Support). Chest compressions produce blood circulation as the result of a generalized increase in intrathoracic pressure and/or direct compression of the heart. The guidelines state "Blood circulated to the lungs by chest compressions will likely receive enough oxygen to maintain life when the compressions are accompanied by properly performed rescue breathing." A victim can be kept alive using CPR provided the rescuer(s) are able to continue delivering properly performed chest compressions and rescue breaths.

Administering chest compressions and rescue breaths is a very physically demanding task. The quality of chest compressions and rescue breaths delivered can degrade as rescuers become fatigued. When a rescuer is fatigued they may not realize that they are compressing the chest with inadequate force.

Administering CPR is a very physically demanding procedure which is performed under stressful (i.e. life and death) circumstances. Under these circumstances, the rescuer is given the difficult tasks of estimating the time between compression's, and the distance which the chest is being compressed. Much of the difficulty in estimating the distance which the chest is being compressed stems from the relative position of the rescuer and the victim. When performing chest compression's, the rescuer positions his or her shoulders directly above the victim's chest, and pushes straight down on the sternum. In this position, the rescuer's line of sight is straight down at the victim's chest. With this line of sight, the rescuer has no visual reference point to use as a basis for estimating the distance that he or she is compressing the chest.

For this reason, there is a need in the art for a practical device which provides the rescuer with feedback to indicate that the rescuer is using proper compression force and that the rate of compressions is correct. A device of this type will provide rescuers with coaching which will enable them to deliver chest compressions consistently and beneficently. To be practical, this device should be one which is already at the rescue scene so that the rescuer is not required to bring an additional piece of equipment to the scene.

Because AEDs are being widely deployed, they are often present at a rescue scene. Prior art AEDs are only capable of defibrillation. There is a need in the industry for an AED which is capable of aiding a rescuer in administering proper chest compressions to a victim.

SUMMARY OF THE INVENTION

The present invention is an AED which is capable of detecting when a rescuer is performing CPR on a victim. This AED is also capable of providing a rescuer with helpful voice prompts to coach them through a CPR procedure. Rescuers who are trained in the use of AEDs are also trained in cardiopulmonary resuscitation (CPR) and will be able to make ready use of the AED of the present invention. AEDs are presently being widely deployed, and they are often on the scene when CPR is administered.

The present invention substantially meets the aforementioned needs. The present invention provides a sensor for sensing both the force applied to the victim's chest and the frequency with which the compressions are applied in order to assist a rescuer in resuscitating a stricken victim. Feedback, preferably by means of voice prompts, is provided to the rescuer by an emergency electronic device in communication with the sensor in order to optimally time the administration of chest compressions and to deliver a chest compression that provides an optimal amount of compression of the chest.

The present invention is a force sensor, for use in combination with an automated electronic defibrillator (AED), includes a first conductive layer. A second conductive layer is spaced apart from the first conductive layer such that no electrical communication occurs between the first and second conductive layers. Electrical communication means are provided for establishing an electrical communication path between the first and second conductive layers responsive to the application of a force to said electrical communication means.

The present invention includes a method of prompting a rescuer in the application of cardiopulmonary resuscitation to a victim having the steps of:

sensing a force applied by the rescuer to the victim's sternum;

sensing an interval between successive applications of force to the victim's sternum;

comparing the force applied by the rescuer to the victim's sternum to a standard of force known to effect resuscitation;

providing a prompt to the rescuer that prompts the rescuer to vary the force delivered to approximate the force that is known to effect resuscitation;

comparing the interval between successive applications of force to the victim's sternum to a standard interval known to effect resuscitation; and providing a prompt to the rescuer that prompts the rescuer to vary the interval of force application to approximate the interval that is known to effect resuscitation.

BRIEF DESCRIPTION OF THE DRAWINGS

FIG. 4 is a perspective view of the force sensor used in conjunction with a pair of electrodes;

FIG. 5 is a perspective view of the force sensor of the present invention applied to a patient;

FIG. 9 is a top plan view of a further embodiment of the force sensor of the present invention;

FIG. 10 is a bottom plan view of the force sensor depicted in FIG. 9;

FIG. 11 is a cross sectional side view of the electrode of the present invention;

FIG. 12 is a cross sectional side view of the electrode of the present invention;

FIG. 13 is a top plan view of a further embodiment of the force sensor of the present invention;

FIG. 14 is a bottom plan view of the force sensor depicted in FIG. 13;

FIG. 15 is a cross sectional side view of the electrode of the present invention;

FIG. 16 is a cross sectional side view of the electrode of the present invention;

FIG. 17 is a top plan view of a further embodiment of the force sensor of the present invention;

FIG. 18 is a bottom plan view of the force sensor depicted in FIG. 17; and

FIG. 19 is a cross sectional side view of the electrode of the present invention.

DETAILED DESCRIPTION OF THE DRAWINGS

Figure 1:
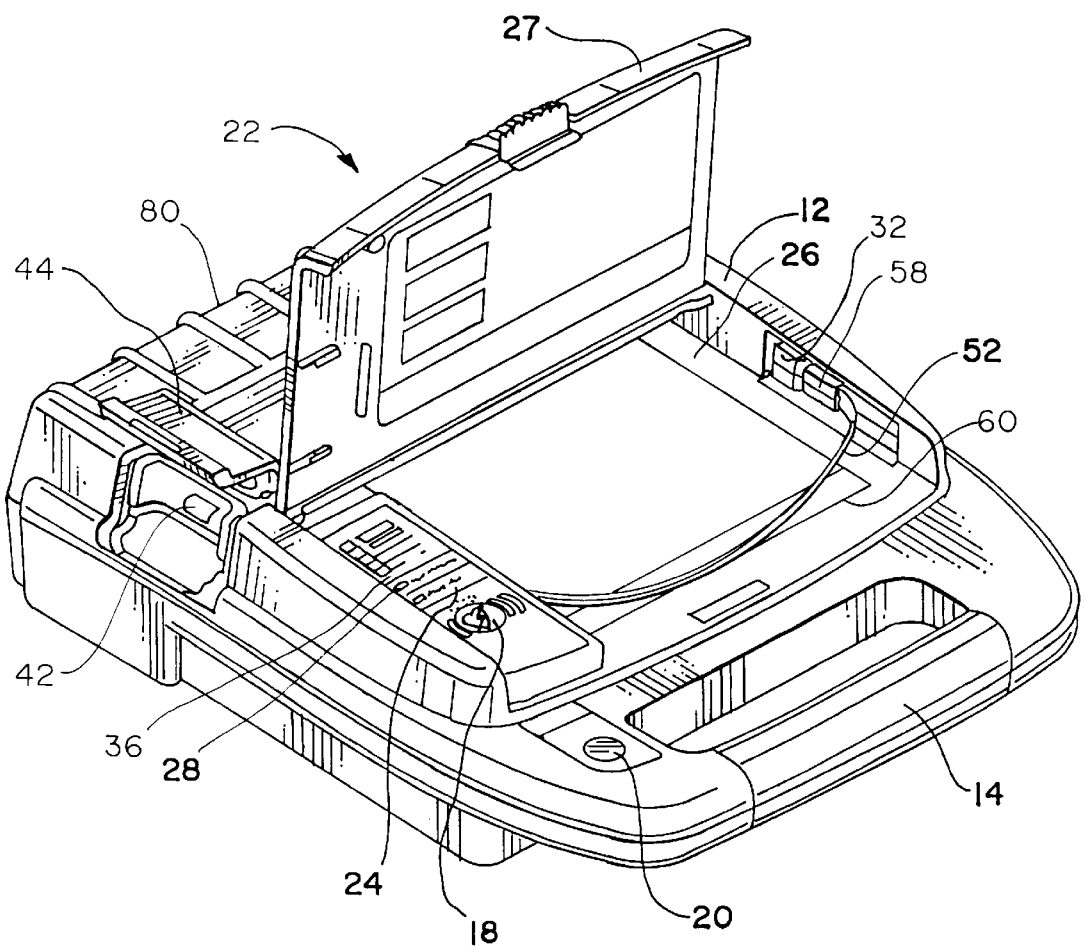
FIG. 1 is a perspective view of an automated external defibrillator.

An AED is shown generally at 22 in FIG. 1. AED 22 is used for emergency treatment of victims of cardiac arrest and is typically used by first responders. AED 22 automatically analyzes a patient's cardiac electrical signal and advises the user to shock a patient upon detection of: (1) ventricular fibrillation; (2) ventricular tachycardia; (3) other cardiac rhythms with ventricular rates exceeding 180 beats per minute and having amplitudes of at lease 0.15 millivolts. When such a condition is detected, AED 22 will build up an electrical charge for delivery to the patient to defibrillate the patient with a defibrillation shock. The operator of AED 22 is guided by voice prompts and an illuminated rescue (shock) button. Olson, et al. U.S. Pat. No. 5,645,571, incorporated herein by reference, discloses the general construction and manner of use of an AED.

AED 22 includes case 12 with carrying handle 14 and battery 80, the battery 80 being removably disposed within a battery compartment (not shown) defined in case 12. Battery 80 functions as an energy source for AED 22. Visual maintenance indicator 20 and data access door 44 are located on the outside of case 12 to facilitate access by the operator. A data communication serial port 42 is situated behind data access door 44. Case 12 also includes panel 24 and electrode compartment 26 defined in a top portion thereof. Panel 24 includes illuminable rescue switch 18 and diagnostic display panel 36 with "electrodes" indicator light 28. Panel 24 and electrode compartment 26 are enclosed by selectively closeable lid 27.

Electrode compartment 26 contains connector 32 and electrode package 60. Electrode compartment 26 hermetically encloses a patient interface which includes a pair of electrodes 50 depicted in FIG. 2, and a force sensor 200, FIGS. 4–16. Electrodes 50 and force sensor 200 are removably connected to connector 32 by lead wires 52 and lead wire connector 58. Electrodes 50 are attachable to a patient prior to a rescue intervention procedure with AED 22.

AED 22 also includes a digital microprocessor-based electrical control system (see the block diagram of FIG. 3) for controlling overall operation of AED 22 and for delivering a defibrillation shock pulse through electrodes 50 via connector 32 and lead wires 52. The electrical control system further includes an impedance measuring circuit for testing the interconnection and operability of electrodes 50 to detect several faults. For example, if the conductive hydrogel adhesive on electrodes 50 is too dry or if electrodes 50 are not properly connected to connector 32 a relatively high impedance (e.g. greater than about 20 ohms) will be present across connector 32. However, when fresh electrodes 50 are properly connected, the impedance across connector 32 will be between about 2 and 10 ohms.

To insure operable electrodes 50, an electrode self-test is conducted (e.g., daily or upon opening lid 27) in which the interconnection and operability of electrodes 50 are checked with the impedance measuring circuit. If electrodes 50 are missing or unplugged from connector 32, if electrodes 50 are damaged, or if the conductive hydrogel adhesive on electrodes 50 is too dry, the control system of AED 22 will illuminate "Electrodes" indicator light 28 on diagnostic display panel 36.

Figure 2:
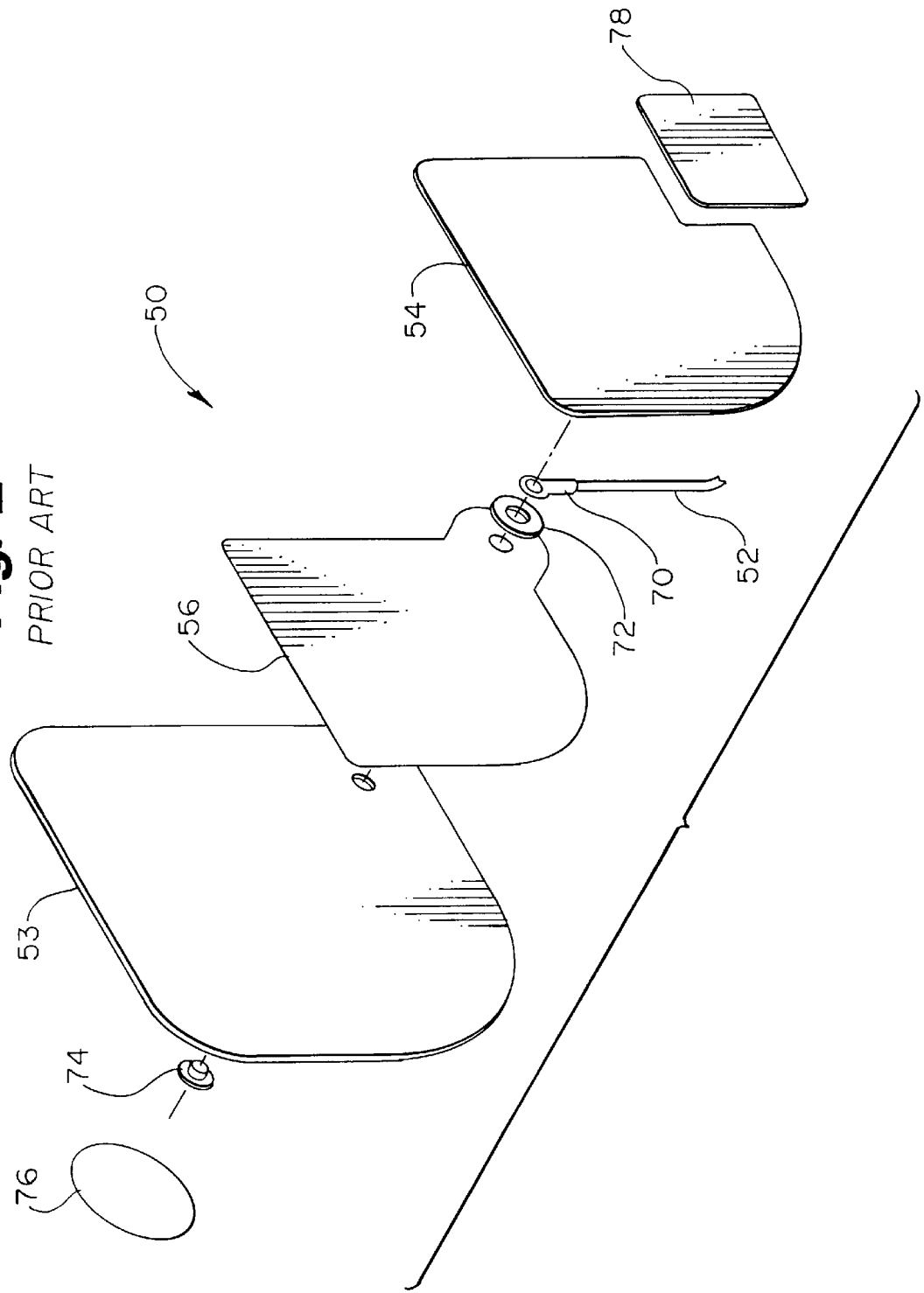
FIG. 2 is an exploded view of an electrode having the force sensor of the present invention.

FIG. 2 is an exploded view of a prior art electrode 50. Electrode 50 includes flexible, adhesive coated backing layer 53 (preferably a polymeric foam), and patient engaging layer 54. Patient engaging layer 54 is preferably a hydrogel material which has adhesive properties and which is electrically conductive. Hydrogel adhesive of this type is commercially available from LecTec Corporation (Minnetonka, Minn.) and Tyco International Ltd. (Hamilton, Bermuda). Current disbursing flexible conductive portion 56 is preferably located between backing layer 53 and patient-engaging hydrogel layer 54. Conductive portion 56, as shown, need not be the same size as backing layer 53 and is preferably a homogeneous, solid, thinly deposited metallic substance, or a conductive ink.

Insulated lead wire 52 is terminated with a wire terminal 70. Wire terminal 70 is electrically connected to conductive portion 56 via conductive rivet 74 and washer 72. Conductive rivet 74 is covered on a first side with insulating disk 76. Conductive rivet 74, washer 72, and wire terminal 70 are all covered on a second side with insulating pad 78. Further examples of electrode pad construction for use with AED 22 are described and shown in U.S. Pat. Nos. 5,697,955, 5,579,919, and 5,402,884, all hereby incorporated by reference.

Figure 3A:
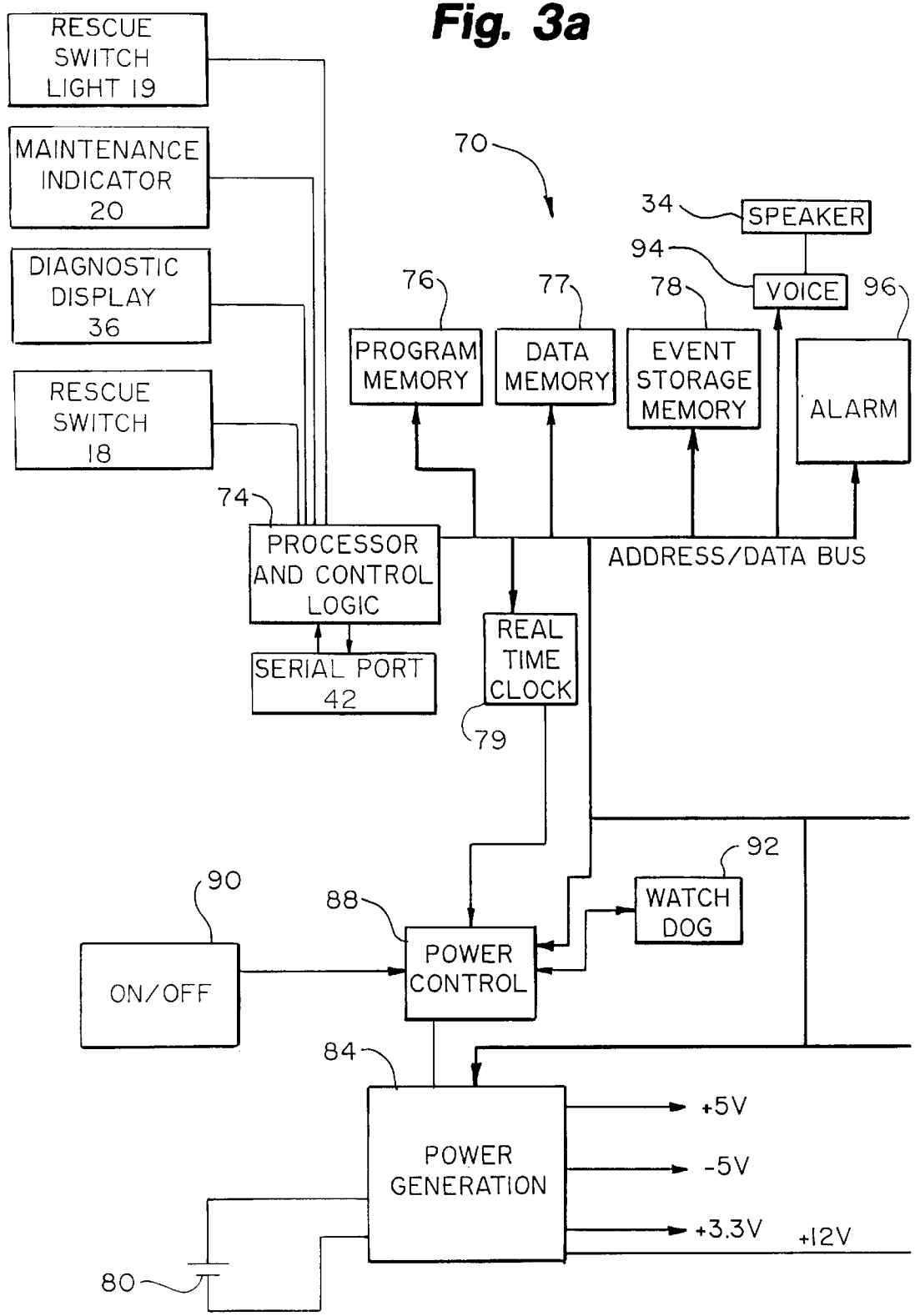
FIG. 3 is a block diagram of an electrical system of the AED.

FIG. 3 is a block diagram of electrical system 70 of AED 22. The overall operation of AED 22 is controlled by a digital microprocessor-based control system 72 which includes a processor 74 interfaced to program memory 76, data memory 77, event memory 78 and real time clock 79. The operating program executed by processor 74 is stored in program memory 76. Electrical power is provided by the battery 80 which is removably positioned within the battery compartment of AED 22 and is connected to power generation circuit 84.

Power generation circuit 84 is also connected to lid switch 90, watch dog timer 92, real time clock 79 and processor 74. Lid switch 90 is a magnetic read relay switch in one embodiment, and provides signals to processor 74 indicating whether lid 27 is open or closed. Data communication port 42 is coupled to processor 74 for two-way serial data transfer using an RS-232 protocol. Rescue switch 18, maintenance indicator 20, the indicator lights of diagnostic display panel 36, the voice circuit 94 and piezoelectric audible alarm 96 are also connected to processor 74. Voice circuit 94 is connected to speaker 34. In response to voice prompt control signals from processor 74, circuit 94 and speaker 34 generate audible voice prompts for consideration by a rescuer.

High voltage generation circuit 86 is also connected to and controlled by processor 74. Circuits such as high voltage generation circuit 86 are generally known, and disclosed, for example, in the commonly assigned Persson et al. U.S. Pat. No. 5,405,361, which is hereby incorporated by reference. In response to charge control signals provided by processor 74, high voltage generation circuit 86 is operated in a charge mode during which one set of semiconductor switches (not separately shown) cause a plurality of capacitors (also not shown), to be charged in parallel to the 12V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient by electrodes 50 through connector 32 connected to the high voltage generation circuit 86.

Impedance measuring circuit 100 is connected to both connector 32 and real time clock 79. Impedance measuring circuit 100 is interfaced to processor 74 through analog-to-digital (A/D) converter 102. Impedance measuring circuit 100 receives a clock signal having a predetermined magnitude from clock 79, and applies the signal to electrodes 50 through connector 32. The magnitude of the clock signal received back from electrodes 50 through connector 32 is monitored by impedance measuring circuit 100. An impedance signal representative of the impedance present across electrodes 50 is then generated by circuit 100 as a function of the ratio of the magnitudes of the applied and received clock signals (i.e., the attenuation of the applied signal).

For example, if electrodes 50 within an unopened package 60 are connected by lead wires 52 and connector 58 is properly connected to connector 32 on AED 22, a relatively low resistance (e.g., less than about 10 ohms) is present across electrodes 50. If the hydrogel adhesive 54 on electrodes 50 is too dry, or the electrodes 50 are not properly positioned on the patient, a relatively high resistance (e.g., greater than about two hundred fifty ohms) will be present across the electrodes 50. The resistance across electrodes 50 will then be between about twenty-five and two hundred fifty ohms when fresh electrodes 50 are properly positioned on the patient with good electrical contacts. It should be noted that these resistance values are given as exemplary ranges and are not meant to be absolute ranges. The impedance signal representative of the impedance measured by circuit 100 is digitized by A/D converter 102 and provided to processor 74.

Impedance measuring circuit 110 is connected to connector 32 and real time clock 79, and is interfaced to processor 74 through analog-to-digital (A/D) converter 102. Impedance measuring circuit 110 receives a clock signal having a predetermined magnitude from clock 79, and applies the signal to force sensor 200 through connector 32. The magnitude of the clock signal received back from force sensor 200 through connector 32 is monitored by impedance measuring circuit 110. An impedance signal representative of the impedance present across force sensor 200 is then generated by circuit 110 as a function of the ratio of the magnitudes of the applied and received clock signals (i.e., the attenuation of the applied signal). The impedance signal representative of the impedance measured by circuit 110 is digitized by A/D converter 102 and provided to processor 74.

FIG. 4 is a plan view of a patient interface 120 for use with AED 22. Patient interface 120 includes connector 58 which is adapted to releasably mate with connector 32 of AED 22. Four lead wires 52A, 52B, 52C, and 52D are all terminated with connector 58. Patient interface 120 also includes a force sensing pad 102 which includes a force sensor 200. Lead wires 52C and 52D are electrically connected to force sensor 200. Electrodes 50A and 50B each include backing layer 53, patient engaging hydrogel layer 54, conductive portion 56, and insulating pad 78.

FIG. 5 is a plan view illustrating patient interface 120 applied to human torso 98 of the victim 112. Force sensing pad 102 is applied over the sternum of torso 98. Force sensing pad 102 may be adhered with pressure sensitive adhesive. Force sensing pad 102 includes force sensor 200 which is electrically connected to lead wires 52C and 52D.

Electrode 50A is shown applied to the upper right chest of torso 98. Electrode 50A is electrically connected to lead wire 52A. Electrode 50B is applied to the lower left side of torso 98 and is electrically connected to lead wire 52B. Lead wires 52A, 52B, 52C, and 52D are terminated with connector 58. Connector 58 is adapted to make releasable, electrical contact with connector 32 of AED 22.

Those skilled in the art will readily recognize that electrodes 50A, 50B and force sensing pad 102 may be placed in locations on torso 98 other than those shown in FIG. 5 without deviating from the spirit or scope of this invention.

Figure 6:
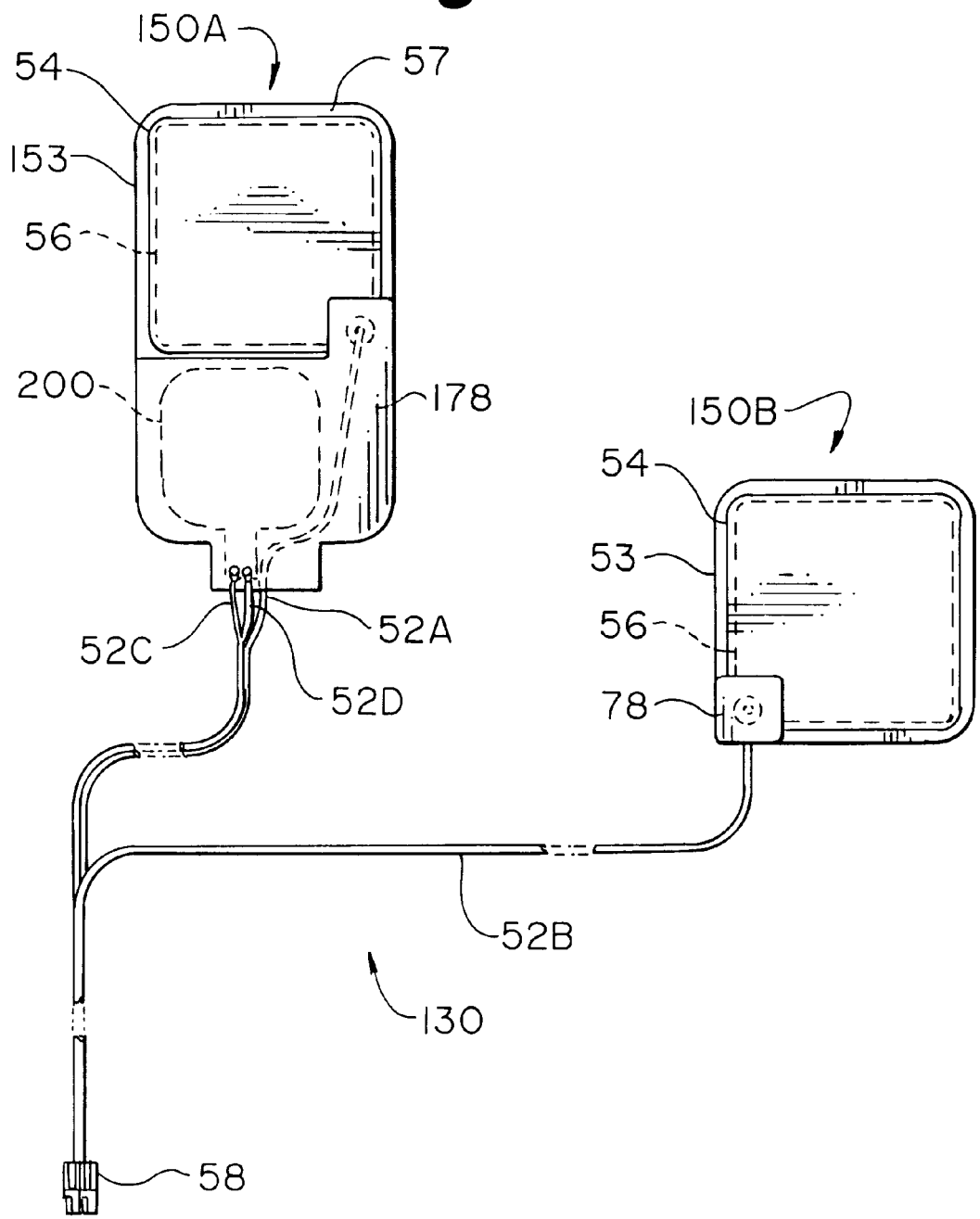
FIG. 6 is a perspective view of an electrode with the force sensor of the present invention disposed therein.

FIG. 6 is a plan view of a patient interface 130 for use with AED 22. Interface 130 includes a second preferred embodiment of force sensor 200. Patient interface 130 includes connector 58 which is adapted to releasably mate with connector 32 of AED 22. Four lead wires 52A, 52B, 52C, and 52D are all terminated with connector 58. Patient interface 130 also includes force sensor 200 which is positioned between backing layer 153 and insulating pad 178 of electrode 150A. Lead wires 52C and 52D are electrically connected to force sensor 200. Electrodes 150A and 150B each include patient engaging hydrogel layer 54, and conductive portion 56.

Figure 7:
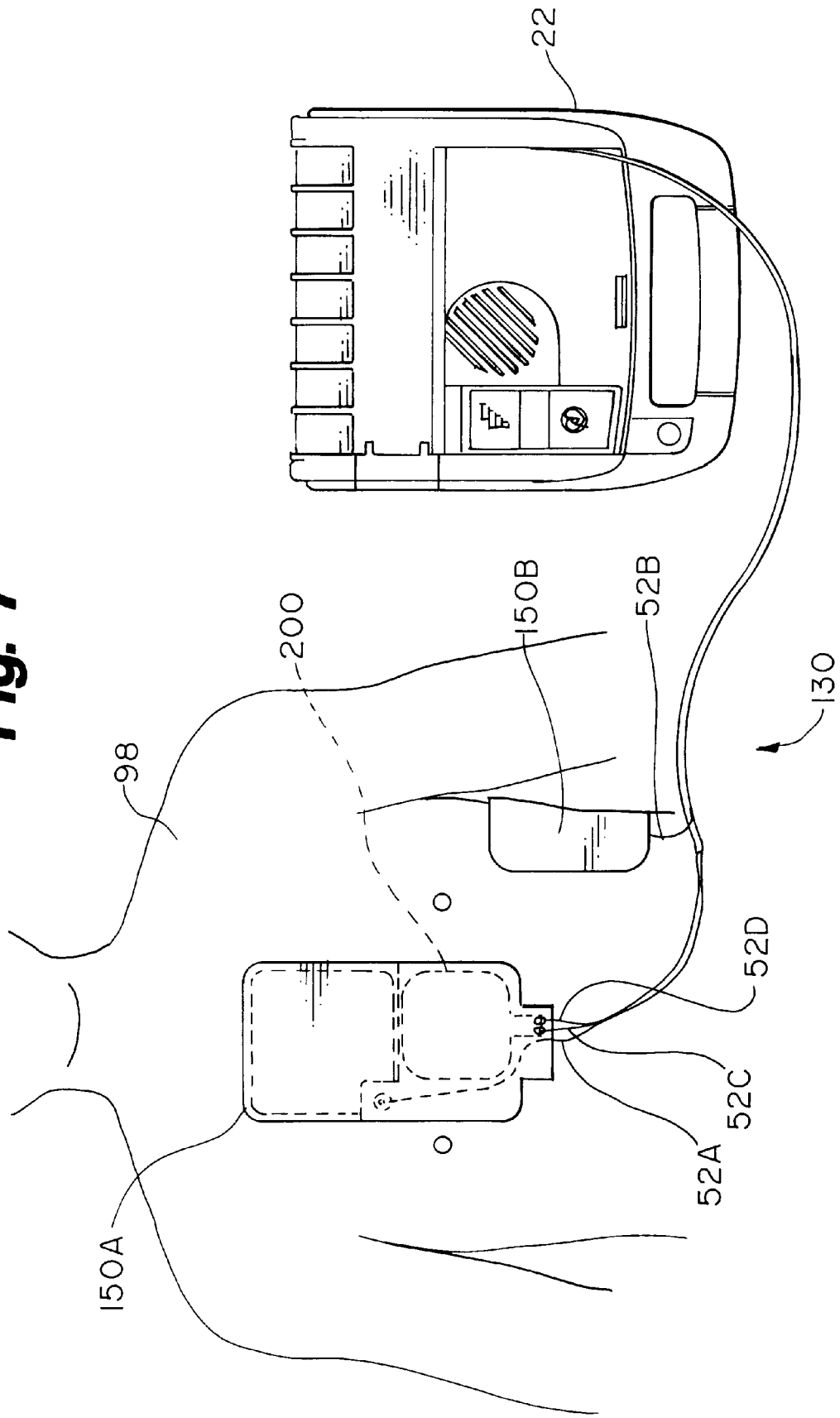
FIG. 7 is a perspective view of the force sensor of FIG. 6 applied to the chest of a victim.

FIG. 7 is a plan view illustrating patient interface 130 applied to torso 98. Force sensor 200 is positioned over the sternum of torso 98. Force sensor 200 is electrically connected to lead wires 52C and 52D. Electrode 150A is shown applied to torso 98. Electrode 150A is electrically connected to lead wire 52A. Electrode 150B is applied to the lower left side of torso 98 and is electrically connected to lead wire 52B. Lead wires 52A, 52B, 52C, and 52D are terminated with connector 58 (not shown). Connector 58 is adapted to make releasable, electrical contact with connector 32 (not shown) of AED 22.

Figure 8:
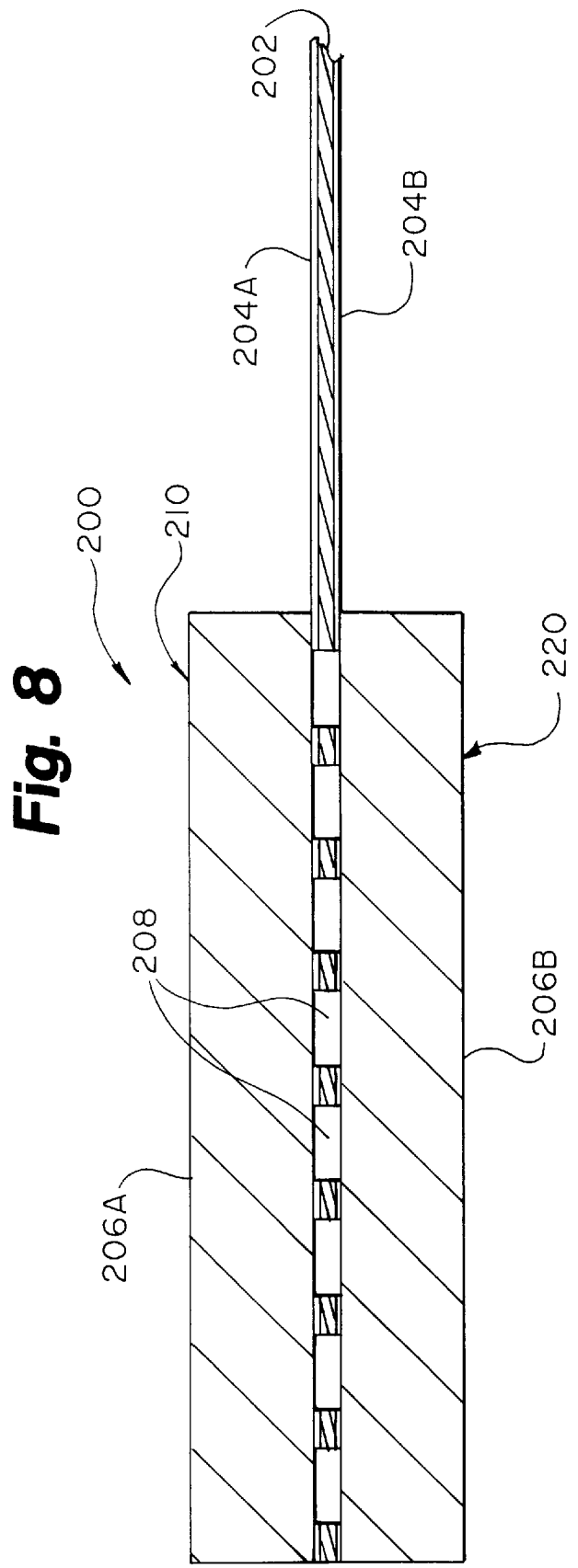
FIG. 8 is a cross sectional side view of the electrode of the present invention.

FIG. 8 is a cross section illustrating an embodiment of a force sensor 200. Force sensor 200 has a first side 210 and a second side 220. Force sensor 200 includes a substrate 202. A conductive pattern 204A, 204B is situated on each side of the substrate layer. Substrate 202 may be any thin (e.g. about 0.002" to 0.020") nonconductive sheet of material. Plastic film materials such as polyester, polycarbonate, PVC, etc. have been found to work well as substrate 202. Conductive patterns 204A, 204B may be any conductive material such as copper foil, nickel foil, or conductive ink. In a preferred embodiment substrate 202 is 5 mil polyester and conductive patterns 204A, 204B are silver conductive ink.

Substrate 202 includes apertures 208. Conductive pads 206A and 206B are situated on each side of substrate 202 as shown in FIG. 8. Conductive pads 206A, 206B are preferably made of a deformable, conductive material. Materials which have been found suitable include conductive silicone rubber, conductive foam rubber, and conductive urethane rubber.

FIG. 9 is a plan view illustrating first side 210 of force sensor 200 with conductive pads 206A, 206B removed. Conductive pattern 204A is seen situated on substrate 202. Apertures 208 are cut through conductive pattern 204A, substrate 202, and conductive pattern 204B, underlying substrate 202.

FIG. 10 is a plan view illustrating second side 220 of force sensor 200 with conductive pads 206A, 206B removed. Conductive pattern 204B is seen situated on substrate 202. As also shown in FIG. 9, apertures 208 are cut through conductive pattern 204B, substrate 202, and conductive pattern 204A, underlying substrate 202.

Referring now to both FIG. 9 and FIG. 10, conductive patterns 204A, 204B each include conductive traces 212A, 212B. Wire terminals 214A, 214B are arranged make electrical contact with conductive traces 212A, 212B respectively. Wire terminals 214A, 214B are attached to substrate 202 with rivets 216A, 216B and washers 218A, 218B. Lead wires 222A, 222B are terminated with wire terminals 214A, 214B.

Those with skill in the art will recognize that other methods may be used to attach lead wires 222A, 222B to conductive traces 212A, 212B. Possible methods include soldering, the use of a connector designed to mate with flexible circuits, and the use of conductive adhesive.

FIG. 11 is a section view of force sensor 200 with a compressive force F applied. When force sensor 200 is used, it is placed between two objects, such as the sternum of a cardiac arrest victim and the heel of a rescuer's hand. When the rescuer presses down with the heel of his or her hand, the force results in pressure distributed across the area of the heel of his or her hand.

When pressure is applied to force sensor 200, conductive pads 206A, 206B extrude through apertures 208. When pads 206A, 206B contact each other, they complete an electrical circuit between conductive layer 204A and conductive layer 204B. Increasing the force F applied to force sensor 200 increases the surface area of the electrical connection between conductive pads 206A, 206B, thereby decreasing the electrical resistance between pads 206A, 206B. The electrical resistance of the circuit between conductive layer 204A and conductive layer 204B is therefore indicative of the magnitude of the force F applied to force sensor 200.

FIGS. 12–14 illustrate a further preferred embodiment of force sensor 200. Force sensor 200 includes a first substrate 222. A conductive pattern 224 is situated on first substrate 222. As in the previous embodiment, substrate 222 may be any thin (e.g. about 0.002" to 0.010") nonconductive sheet of material. Plastic film materials such as polyester, polycarbonate, PVC, etc. have been found to work well as substrate 222. Conductive pattern 224 may be any conductive material such as copper foil, nickel foil, or conductive ink. In a preferred embodiment substrate layer 222 is 5 mil polyester and conductive pattern 224 is silver conductive ink.

Force sensor 200 includes second substrate 226. A conductive pattern 228 is situated on second substrate 226. Second substrate 226 is situated on first substrate 222. First substrate 222 and second substrate 226 may be held together with a layer of pressure sensitive adhesive (not shown).

Substrate 222 includes apertures 230. A conductive pad 232 is situated on, and makes electrical contact with conductive pattern 224 as shown in FIG. 14. Conductive pad 232 is preferably made of a deformable, conductive material. Materials which have been found suitable include conductive silicone rubber, conductive foam rubber, and conductive urethane rubber.

FIG. 13 is a plan view illustrating second substrate 226 and conductive pattern 228.

FIG. 14 is a plan view illustrating first substrate 222 and conductive pattern 224.

FIG. 15 is a section view of the force sensor 200 of FIG. 12 with a force F applied. When force sensor 200 is used, it is placed between two objects, such as the sternum of a cardiac arrest victim and the heel of a rescuers hand. When the rescuer presses down with the heel of his or her hand, the force results in pressure distributed across the area of the heel of his or her hand.

When a force F is applied to force sensor 200, conductive pad 232 extrudes through apertures 230. When conductive pad 232 contacts conductive pattern 228 it completes an electrical circuit between conductive pattern 224 and conductive pattern 228. Increasing the force F applied to force sensor 200 increases the surface area of the electrical connection between conductive pads 232 and conductive pattern 228, thereby reducing the electrical resistance between pad 232 and pattern 228. Accordingly, change in contact area creates a change in electrical resistance which is indicative of the force applied to force sensor 200.

FIGS. 16–18 illustrate another third embodiment of force sensor 200. In this embodiment force sensor 200 includes a first substrate 242. Two conductive patterns 244A, 244B are situated on first substrate 242.

Force sensor 200 includes second substrate 246 which includes apertures 250. Second substrate 246 is comprised of a non-conductive material. Polyester, polyethylene, and polypropylene have been found to be suitable materials for second substrate 246. A conductive pad 252 is situated on second substrate 246. As in the previous embodiments, conductive pad 232 is preferably made of a deformable, conductive material.

FIG. 17 is a plan view illustrating first substrate 242 and conductive patterns 244A, 244B. The conductive patterns 244A, 244B are arranged so that they are in close proximity to each other. Small gaps 256 are left between conductive paths 244A, 244B so that there is no direct electrical contact between conductive paths 244A, 244B.

FIG. 18 is a plan view illustrating second substrate 246 and apertures 250.

FIG. 19 is a section view of the force sensor 200 of FIGS. 16–18 with a force F applied. When force sensor 200 is used, it is placed between two objects, such as the sternum of a cardiac arrest victim and the heel of a rescuers hand. When the rescuer presses down with the heel of his or her hand, the force F results in pressure distributed across the area of the heel of his or her hand.

When pressure is applied to force sensor 200, conductive pad 252 extrudes through apertures 250. When conductive pad 252 contacts conductive patterns 244A, 244B it completes an electrical circuit between conductive pattern 244A and conductive pattern 244B. Increasing the force applied to force sensor 200 increases the surface area of the electrical connection between conductive pad 252 and conductive patterns 244A, 244B. This change in contact area creates a change in electrical resistance which is indicative of the force applied to force sensor 200.

Referring to FIGS. 4 and 5 in operation force sensor 200 is positioned on the sternum of a victim 112. The rescuer places the heel of his or her hand onto force sensor 200 and delivers chest compressions to the chest of the victim 112. Force sensor 200 and impedance measuring circuit 110 produce an electrical signal proportional to the force applied to the victim's chest. This signal indicates to processor 74 the rate and magnitude of the chest compressions which the victim 112 is receiving. This signal also allows processor 74 to determine the precise time that a rescuer has begun (or stopped) CPR.

Processor 74 compares the measured rate of chest compressions to a range of desired values.

If the current chest compression rate value delivered by the rescuer is less than the desired range, processor 74 will produce a control signal which causes voice circuit 94 and speaker 34 to generate an appropriate voice prompt such as "faster". If the current chest compression rate value is greater than the desired range, processor 74 will produce a control signal which causes voice circuit 94 and speaker 34 to generate an appropriate voice prompt such as "slower".

Processor 74 also compares the measured chest compression force to a range of desired values. If the chest compression force delivered by the rescuer is less than the desired range, processor 74 will produce a control signal which causes voice circuit 94 and speaker 34 to generate an appropriate voice prompt such as "harder". If the chest compression force is greater than the desired range, processor will produce a control signal which causes voice circuit 94 and speaker 34 to generate an appropriate voice prompt such as "softer".

AED 22 may also provide other types of audible feedback to the rescuer. For example, AED 22 may give an audible signal each time the force measured using force sensor 200 reaches a desired value.

The present invention may be embodied in other specific forms without departing from the spirit of the essential attributes thereof. Therefore, the illustrated embodiments should be considered in all respects as illustrative and not restrictive, reference being made to the appended claims rather than to the foregoing description to indicate the scope of the invention.

What is claimed is:

1. An automated electronic defibrillator (AED) for use by an operator in assisting in resuscitating a victim, comprising:
    a force sensor applicable to a skin surface of the victim and being responsive to the application of a force to said force sensor,
    an AED control system being in electrical communication with the force sensor, the AED control system processing a signal communicated from the force sensor related to the magnitude of force applied thereto and to the frequency of application of the force thereto; and
    AED prompting means operably coupled to the AED control system for receiving communication signals from the AED control system and for communicating prompts to the operator for use by the operator in resuscitating the victim, the prompts being related to the signal communicated to the AED control system by the force sensor related to the magnitude of force applied to the force sensor and to the frequency of application of the force to the force sensor.

2. The AED of claim 1 wherein the force sensor is responsive to the relative magnitude of the force applied thereto and communicates a signal related to said force magnitude to the AED control system.

3. The AED of claim 2 wherein the AED control system communicates signals relating to the relative magnitude of force applied to the force sensor to the AED prompting means for transmission as a prompt to the rescuer.

4. The AED of claim 1 wherein the AED control system determines the interval between a succession of force applications applied to the force sensor.

5. The AED of claim 4 wherein the AED control system communicates signals relating to the interval between a succession of force applications applied to the force sensor to the AED prompting means for transmission as a prompt to the rescuer.

6. The AED of claim 1 wherein the force sensor comprises:
    a first conductive layer;
    a second conductive layer being spaced apart from the first conductive layer, the first and second conductive layers being electrically isolated from one another; and
    electrical communication means for establishing electrical communication between the first and second conductive layers responsive to the application of a force to said electrical communication means.

7. The AED of claim 6 wherein at least a part of the electrical communication means of the force sensor are formed of an extrudable, electrically conductive material, the electrical communication means being extruded by the application of a force to said electrical communication means, at least one extrusion thereof establishing a path of electrical communication between the first and second conductive layers responsive to the application of said force.

8. The AED of claim 7, the force sensor further including a flexible, nonconductive layer being disposed between the first and second conductive layers.

9. The AED of claim 8 wherein the first and second conductive layers of the force sensor are formed of conductive ink printed on opposed sides of the nonconductive layer.

10. The AED of claim 9, the force sensor further including a plurality of holes defined through the nonconductive layer and through the first and second conductive layers printed thereon.

11. The AED of claim 10, the force sensor further including a first extrudable, conductive layer disposed on the first conductive layer and a second extrudable, conductive layer disposed on the second conductive layer, the first and second extrudable, conductive layers being extrudable into the plurality of holes defined through the nonconductive layer and through the first and second conductive layers responsive to a force applied thereto to form an electrically communicative connection between the first and second conductive layers.

12. The AED of claim 6 wherein the first and second conductive layers of the force sensor are formed of conductive, metallic foil.

13. The AED of claim 1 wherein the force sensor is disposed in a hole defined in an electrode.

14. The AED of claim 6 wherein the magnitude of the force applied to the force sensor is inversely proportional to the impedance existing between the first and second conductive layers.

15. The AED of claim 6 wherein the impedance existing between the first and second conductive layers of the force sensor is related to the magnitude of the force applied to the force sensor.

16. A method of prompting a rescuer in the application of cardiopulmonary resuscitation to a victim comprising the steps of:
    sensing a force applied by the rescuer to the victim by means of a force sensor;
    sensing an interval between successive applications of force to the victim's sternum; by means of a processor operably coupled to the force sensor;

the processor comparing the force applied by the rescuer to the victim's sternum to a standard of force known to effect resuscitation;

the processor providing a prompt to the rescuer that prompts the rescuer to vary the force delivered to approximate the force that is known to effect resuscitation;

the processor comparing the interval between successive applications of force to the victim's sternum to a standard interval known to effect resuscitation; and the processor providing a prompt to the rescuer that prompts the rescuer to vary the interval of force application to approximate the interval that is known to effect resuscitation.

17. An automated electronic defibrillator (AED) for use by an operator in assisting in resuscitating a victim, having a charging circuit for developing a high voltage charge, at least two electrodes for application to the person of a victim, the at least two electrodes being in electrical communication with the charging circuit, a control circuit communicatively coupled to the charging circuit and the electrodes for detecting certain biological parameters of the victim and for controlling the delivery of a voltage charge from the charging circuit through the at least two electrodes to the victim, comprising:

means for prompting a rescuer in the delivery of cardiopulmonary resuscitation (CPR) to the victim, the means for prompting a rescuer further including the control system being in electrical communication with a force sensor, the AED control circuit processing a signal communicated from the force sensor related to the magnitude of force applied thereto and to a frequency of application of the force thereto.

18. The AED of claim 17 wherein the means for prompting a rescuer includes a force sensor applicable to a skin surface of the victim and being responsive to the application of a force to said force sensor.

19. The AED of claim 17 wherein the means for prompting a rescuer further includes prompting means operably coupled to the AED control circuit for receiving communication signals from the AED control circuit and for communicating prompts to the rescuer for use by the rescuer in resuscitating the victim, the prompts being related to the signal communicated to the AED control circuit by a force sensor related to the magnitude of force applied to the force sensor and to the frequency of application of the force to the force sensor.

20. The AED of claim 19 wherein the force sensor is responsive to the relative magnitude of the force applied thereto and communicates a signal related to said force magnitude to the AED control system.

21. The AED of claim 20 wherein the AED control circuit communicates signals relating to the relative magnitude of force applied to the force sensor to the AED prompting means for transmission as a prompt to the rescuer.

22. The AED of claim 21 wherein the AED control system determines the interval between a succession of force applications applied to the force sensor.

23. The AED of claim 22 wherein the AED control circuit communicates signals relating to the interval between a succession of force applications applied to the force sensor to the AED prompting means for transmission as a prompt to the rescuer.

24. An automated electronic defibrillator (AED) for use by an operator in assisting in resuscitating a victim, having a charging circuit for developing a high voltage charge, at least two electrodes for application to the person of a victim, the at least two electrodes being in electrical communication with the charging circuit, a control circuit communicatively coupled to the charging circuit and the electrodes for detecting certain biological parameters of the victim and for controlling the delivery of a voltage charge from the charging circuit through the at least two electrodes to the victim, comprising:

means for prompting a rescuer in the delivery of cardiopulmonary resuscitation (CPR) to the victim, the means for prompting a rescuer including a force sensor applicable to a skin surface of the victim and being responsive to the application of a force to said force sensor, the force sensor having, a first conductive layer;

a second conductive layer being spaced apart from the first conductive layer, the first and second conductive layers being electrically isolated from one another; and electrical communication means for establishing electrical communication between the first and second conductive layers responsive to the application of a force to said electrical communication means.

25. The AED of claim 24 wherein at least a part of the electrical communication means of the force sensor are formed of an extrudable, electrically conductive material, the electrical communication means being extruded by the application of a force to said electrical communication means, at least one extrusion thereof establishing a path of electrical communication between the first and second conductive layers responsive to the application of said force.

26. The AED of claim 25, the force sensor further including a flexible, nonconductive layer being disposed between the first and second conductive layers.

27. The AED of claim 26 wherein the first and second conductive layers of the force sensor are formed of conductive ink printed on opposed sides of the nonconductive layer.

* * * * *